United States Patent [19]

Ataka et al.

[11] Patent Number: 4,831,190
[45] Date of Patent: May 16, 1989

[54] TRIFLUOROHYDROXYAROMATIC ACID AND PREPARATION THEREOF

[75] Inventors: Kikuo Ataka; Masayoshi Oku, both of Ube, Japan

[73] Assignee: UBE Industries, Ltd., Ube, Japan

[21] Appl. No.: 126,173

[22] Filed: Nov. 27, 1987

[30] Foreign Application Priority Data

Dec. 4, 1986 [JP] Japan .................. 61-287763
Dec. 8, 1986 [JP] Japan .................. 61-290399

[51] Int. Cl.$^4$ ............................. C07C 65/04
[52] U.S. Cl. ...................... 362/474; 560/53; 560/59; 544/102
[58] Field of Search ........................ 562/474

[56] References Cited

PUBLICATIONS

Ishikawa, N. et al. Nippon Kagaku Kaishi(1) 200–2 1976, CA85(5): 32584g.

Primary Examiner—Paul J. Killos
Attorney, Agent, or Firm—Frishauf, Holtz, Goodman & Woodward

[57] ABSTRACT

There are disclosed 2,4,5-Trifluoro-3-hydroxybenzoic acid represented by the following formula (I):

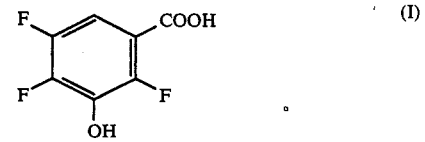

and a salt thereof and a process for preparing the same.

Further, there is disclosed a process for preparing 3,5,6-trifluoro-4-hydroxyphthalic acid, which is employed for preparing the above compound.

14 Claims, No Drawings

TRIFLUOROHYDROXYAROMATIC ACID AND PREPARATION THEREOF

BACKGROUND OF THE INVENTION

This invention relates to a trifluorohydroxyaromatic acid and preparetion thereof, more particularly to a novel substance 2,4,5-trifluoro-3-hydroxybenzoic acid useful as the synthetic intermediate for the quinolone carboxylic acid type antibacterial agent and a process for producing the same, and further to a process for preparing 3,5,6-trifluoro-4-hydroxyphthalic acid useful as the precursor of 2,4,5-trifluoro-3-hydroxybenzoic acid.

In the prior art, as the synthetic antibacterial agent, there have been known developed nalidixic acid represented by the following formula:

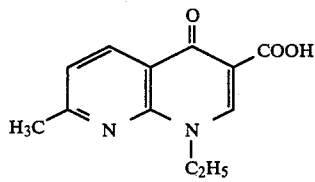

pipemidic acid represented by the following formula:

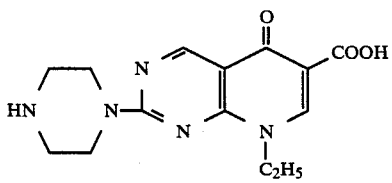

piromidic acid represented by the following formula:

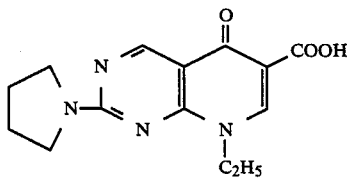

Norfloxacin represented by the following formula:

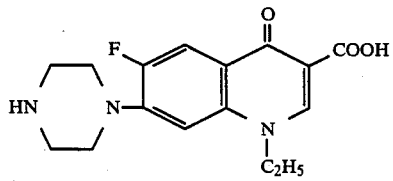

etc., and have been provided for therapy of various infectious diseases.

Further, as the compound which improves various characteristics of the above antibacterial agents, quinolone carboxylic acid type antibacterial agents, having oxygen atom at the 8-position have been developed (for example, Japanese Patent Publication No. 11955/1986).

However, a large number of steps are required for synthesis of a quinolone carboxylic acid derivative having oxygen atom at the 8-position, and it has been desired to shorten the preparation steps.

2,4,5-Trifluoro-3-hydroxybenzoic acid represented by the following formula (I) may be considered to be useful as the synthetic intermediate for the above quinolone carboxylic acid derivative:

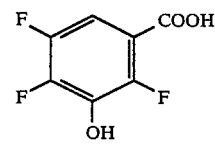

However, even if a nucleophilic reagent such as RO$^-$ or OH$^-$ may be reacted with 2,3,4,5-tetrafluorobenzoic acid, no nucleophilic reaction to the meta-position of the carboxylic group occurs, but the reaction occurs all selectively with the para-position and the ortho-position to give no 2,4,5-trifluoro-3-hydroxybenzoic acid. Also, according to other methods, no 2,4,5-trifluoro-3-hydroxybenzoic acid has been obtained.

It can be expected that 3,5,6-trifluoro-4-hydroxyphthalic acid is useful as the precursor of 2,4,5-trifluoro-3-hydroxybenzoic acid.

A process for preparing 3,5,6-trifluoro-4-hydroxyphthalic acid used here as the starting material is described in Osadchii, S. A., Bakahash, V. A.; Zh. Org. Khim., Vol. 6 (8), p. 1636 (1970) (Chemical Abstract, 73, 109544p). According to this litrature, when tetrafluorophthalic anhydride and pentafluorophenylacetic acid are reacted in triethylamine-acetic anhydride, a triethylamine salt of 5-hydroxy-4,6,7-trifluoro-3-(pentafluorobenzylidene)phthalide is obtained. And, by treatment of the by-products of this reaction, 3,5,6-trifluoro-4-hydroxyphthalic acid is obtained.

However, this process obtains 3,5,6-trifluoro-4-hydroxyphthalic acid as the accompanying reaction product, its yield is low and also the reactions are cumbersome.

Also, Ishikawa, Suzuki, Tanabe, et al. report a method for synthesis of dimethyl 3,5,6-trifluoro-4-methoxyphthalate in Journal of Chemical Society of Japan, p. 200 (1976). From this compound, according to a known method (for example, after converted to 3,5,6-trifluoro-4-methoxyphthalic acid by hydrolysis with an aqueous alkali solution, reacted with a strong acid such as hydrobromic acid), 3,5,6-trifluoro-4-hydroxyphthalic acid can be obtained.

However, this method obtains dimethyl 3,5,6-trifluoro-4-methoxyphthalate by the reaction after tetrafluorophthalic acid is once converted to a methyl ester, and the three methyl groups are required to be eliminated for obtaining the objective 3,5,6-trifluoro-4-hydroxyphthalic acid. Thus, it can be hardly said to be a rational method.

The present inventors, in view of the state of the art as described above, have intensively studied about an industrial process for preparing 2,4,5-trifluoro-3-hydroxybenzoic acid and its precursor, 3,5,6-trifluoro-4-hydroxyphthalic acid to accomplish the present invention.

SUMMARY OF THE INVENTION

The present invention concerns a novel compound 2,4,5-trifluoro-3-hydroxybenzoic acid of the following formula (I) and its salt, and also a process for production of the same.

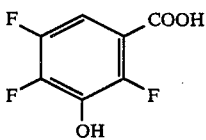

(I)

The compound of the present invention can be prepared, for example, as follows.

That is, the objective compound can be obtained by treating a compound represented by the following formula (II):

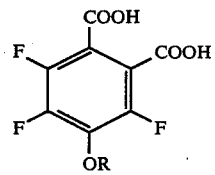

(II)

wherein R represents a hydrogen atom or an organic group capable of forming a hydroxyl group by hydrolysis,
in water or an aqueous solvent at 80° to 230° C. under naturally occurring pressure.

Also, the process for preparing 3,5,6-trifluoro-4-hydroxyphthalic acid which is used for preparation of the above compound (II) where R is a hydrogen atom comprises allowing 3,4,5,6-tetrafluorophthalic acid to react with an alkaline compound in water or an aqueous solvent at 70° to 120° C., and then treating the reaction product with an acidic aqueous solution.

DESCRIPTION OF THE PREFERRED EMBODIMENTS

In the above reaction for obtaining 2,4,5-trifluoro-3-hydroxybenzoic acid, when R in the starting compound (II) is an organic group, the present reaction gives first 3,5,6-trifluoro-4-hydroxyphthalic acid, and then gives the objective compound (I) through selective decarbonization only of the carboxylic group at the para-position relative to the hydroxyl group. Accordingly, the organic group as R in the above formula (II) may be any group capable of forming a hydroxyl group by hydrolysis, but particularly it may be preferably an alkyl group having 1 to 6 carbon atoms, an aralkyl group having 7 to 10 carbon atoms, a cycloalkyl group having 5 to 10 carbon atoms or an acyl group having 1 to 10 carbon atoms.

Examples of the above alkyl group having 1 to 6 carbon atoms may include a methyl group, an ethyl group, a propyl group, an isopropyl group, a butyl group, an isobutyl group, a sec-butyl group, a tert-butyl group, a pentyl group, a hexyl group, and the like.

The above aralkyl group having 7 to 10 carbon atoms may be, for example, a benzyl group, a p-chlorophenylmethyl group, etc.

The above cycloalkyl group having 5 to 10 carbon atoms may be, for example, a cyclopentyl group, a cyclohexyl group, etc.

The above acyl group having 1 to 10 carbon atoms may be exemplified by a formyl group, an acetyl group, a benzoyl group, a propionyl group, a butynyl group, and the like.

Specific examples of the starting compound (II) may include 3,5,6-trifluoro-4-hydroxyphthalic acid, 3,5,6-trifluoro-4-methoxyphthalic acid, 3,5,6-trifluoro-4-ethoxyphthalic acid, 3,5,6-trifluoro-4-propoxyphthalic acid, 3,5,6-trifluoro-4-butoxyphthalic acid, 3,5,6-trifluoro-4-benzyloxyphthalic acid, 3,5,6-trifluoro-4-acetoxyphthalic acid, 3,5,6-trifluoro-4-benzoyloxyphthalic acid, and the like.

The synthetic method of such starting compounds (II) is described in, for example, Ishikawa et al., The Journal of Chemical Society of Japan, p. 200 (1976).

In the preparation process of the present invention, the amount of the solvent may be preferably within the range of 3 to 100-fold by weight relative to the starting compound (II). As the aqueous solvent, water and a mixture of water with a solvent which can be dissolved in water at any ratio and does not react under acidic conditions can be used. Specific examples of aqueous solvents may include mixtures of alcohols such as methanol, ethanol, etc., ethers such as dioxane, etc., with water. The content of water is preferably 10% or higher. The reaction is carried out at a temperature within the range of from 80° to 230° C. under naturally occurring pressure, and more preferably the reaction temperature is preferably within the range of from 100° to 190° C. The reaction time is dependent on the reaction temperature, but the reaction is generally completed within 0.5 to 20 hours. The present invention may be also carried out in the presence of an inert gas such as nitrogen and argon.

The reaction product can be isolated according to a conventional method such as filtration, etc., because the reaction mixture, after cooling, can be concentrated to precipitate the product as crystal or powder.

As the salt of the compound (I) of the present invention may include, for example, those selected from the group consisting of a lithium salt, sodium salt, potassium salt and calcium salt.

Next, the process for preparing 3,5,6-trifluoro-4-hydroxyphthalic acid which can be used as the starting material for preparing the above 2,4,5-trifluoro-3-hydroxybenzoic acid of the present invention is to be described.

Examples of the alkaline compound may include, for example, alkali metal hydroxides such as lithium hydroxide, sodium hydroxide, potassium hydroxide and cesium hydroxide; hydrogen carbonates such as potassium hydrogen carbonate and sodium hydrogen carbonate; etc. Industrially, it is preferable to use sodium hydroxide or potassium hydroxide. The amount of the alkaline compound is theoretically required to be 4 moles or more per 1 mole of tetrafluoroacetic acid. The concentration of the alkaline compound in the reaction mixture is preferably within the range of from 5 to 40% by weight.

The present reaction is carried out in water or an aqueous solvent, and the amount of the solvent may be preferably within the range of from 3 to 100-fold by weight relative to tetrafluoroacetic acid. As the aqueous solvent, water and a mixture of water with a solvent which can be dissolved in water at any desired ratio and does not react under alkaline conditions can be used. Specific examples of aqueous solvents may include mixtures of alcohols such as methanol, ethanol, etc., ethers such as dioxane, etc., with water. The content of water is preferably 10% or higher. The reaction temperature may be 70° to 120° C., preferably 80° to 95° C. The reaction time is dependent on the reaction temperature, but the reaction is generally completed within 0.5 to 20 hours.

If the reaction temperature is lower than 70° C., the reaction is remarkably slow, while when it exceeds 120° C., by-products will be produced in greater amounts, whereby the yield of the alkali salt of 3,5,6-trifluoro-4-hydroxyphthalic acid which is the objective compound will be lowered.

3,5,6-Trifluoro-4-hydroxyphthalic acid is formed by adding an acidic aqueous solution to an aqueous solution of the salt of 3,5,6-trifluoro-4-hydroxyphthalic acid obtained to pH 1 to 4. As the acid, any acid which can neutralize alkalinity may be used and, for example, an aqueous solution of sulfuric acid, hydrochloric acid can be used. After the acid precipitation, 3,5,6-trifluoro-4-hydroxyphthalic acid can be isolated by, for example, extracting it in an organic layer by use of a solvent such as ether, ethyl acetate, etc., and after the liquid separation evaporating the solvent to dryness. The 3,5,6-trifluoro-4-hydroxyphthalic acid thus obtained is a white substance of high purity.

EXAMPLES

The present invention is described in more detail by referring to Examples, by which the present invention is not limited at all.

EXAMPLE 1

An amount of 0.84 g of to 3,5,6-trifluoro-4-methoxyphthalic acid and 10 ml of water were placed in a sealed tube, replaced with nitrogen and heated at 190° C. for 8 hours. After completion of the reaction, the mixture was cooled to room temperature and concentrated, whereby crystals were precipitated. The crystals were filtered, washed (chloroform 5 ml) and then dried. As colorless crystals, 0.48 g of 2,4,5-trifluoro-3-hydroxybenzoic acid was obtained.

Yield: 74%.

m.p.: 144° to 146° C.

$^1$H NMR spectrum (in $CD_3OD$) δ ppm: 7.25 (m, 1H, $^3J_{HF}$ 10.74 Hz, $^4J_{HF}$ 8.30 Hz, $^4J_{HF}$ 5.86 Hz) aromatic proton, 4.94 (bs, 1H) hydroxy proton.

Mass analysis: M+ 1.92.

EXAMPLE 2

An amount of 2 g (30.7 mmole) of 86% potassium hydroxide was dissolved in 10 ml of water and heated to 90° C. To this solution, under stirring, was added gradually 1.0 g (4.20 mmole) of 3,4,5,6-tetrafluorophthalic acid, and the reaction was carried out at 90° C. for 9 hours. After left to cool, to the aqueous reaction solution was added concentrated hydroxychloric acid to adjust pH to 2 to give 3,5,6-trifluoro-4-hydroxyphthalic acid. To this was added 15 ml of diethyl ether, and 3,5,6-trifluoro-4-hydroxyphthalic acid was extracted in the organic layer. This extraction operation was repeated for 5 times, and the diethyl ether layers obtained were dried over anhydrous sodium sulfate, then evaporated to dryness and washed with chloroform to give 1.05 g of 3,5,6-trifluoro-4-hydroxyphthalic acid monohydrate.

Yield: 98% m.p.: 171° to 172° C.

$C^{13}$ NMR (in $CD_3OD$) δ ppm: 111.8 (m, C-1), 120.0 (m, C-2), 140.2 (m, C-4), 143.5 (m, $^1J_{CF}$ 249.1 Hz, C-5), 147.1 (m, $^1J_{CF}$ 250.6 Hz, C-3), 147.9 (m, $^1J_{CF}$ 253.5 Hz, C-6), 165.4 and 166.4 (m, COOH).

Mass analysis: M+ 236.

EXAMPLE 3

An amount of 0.47 g of to 3,5,6-trifluoro-4-hydroxyphthalic acid and 10 ml of water were placed in a sealed tube, replaced with nitrogen and heated at 140° C. for 3 hours. After completion of the reaction, the mixture was cooled to room temperature and concentrated, whereby crystals were precipitated. The crystals were filtered, washed (chloroform 5 ml) and then dried. As colorless crystals, 0.35 g of 2,4,5-trifluoro-3-hydroxybenzoic acid was obtained.

Yield: 90%.

m.p.: 144° to 146° C.

$^1$H NMR spectrum (in $CD_3OD$) δ ppm: 7.25 (m, 1H, $^3J_{HF}$ 10.74 Hz, $^4J_{HF}$ 8.30 Hz, $^4J_{HF}$ 5.86 Hz) aromatic proton, 4.94 (bs, 1H) hydroxy proton.

Mass analysis: M+ 192.

REFERENCE EXAMPLE

By using 2,4,5-trifluoro-3-hydroxybenzoic acid as a starting material, ethyl 9,10-difluoro-3-methyl-7-oxo-2,3-dihydro-7H-pyrido[1,2,3-de][1,4]benzoxazine-6-carboxylate (IV) which is an important intermediate for synthesis of an antibacterial agent, ofloxacin (9-fluoro-3-methyl-10-(4-methyl-1-piperazinyl)-7-oxo-2,3-dihydro-7H-pyrido[1,2,3-de][1,4]benzoxazine-6-carboxylic acid) was synthesized following the reaction schemes shown below.

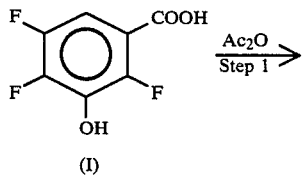

(I)

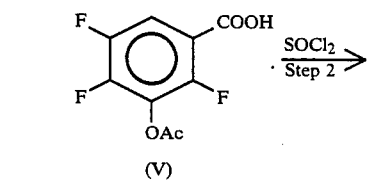

(V)

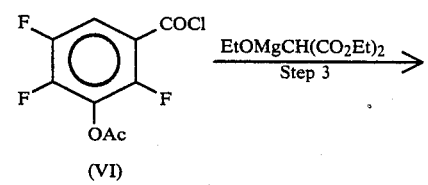

(VI)

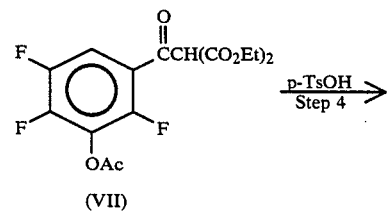

(VII)

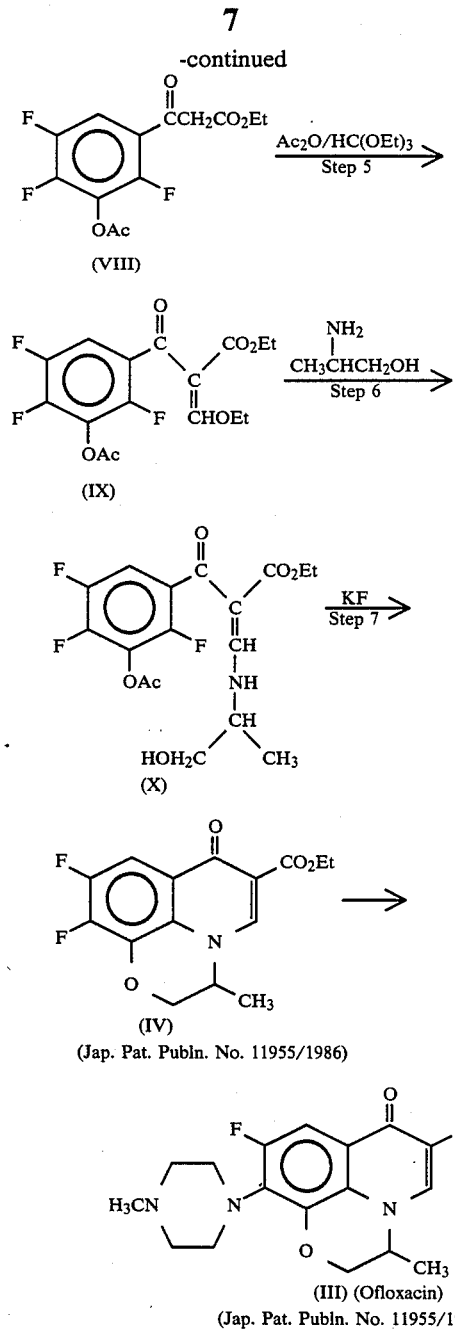

(VIII)

(IX)

(X)

(IV)
(Jap. Pat. Publn. No. 11955/1986)

(III) (Ofloxacin)
(Jap. Pat. Publn. No. 11955/1986)

[Step 1]

To 12.6 g (0.066 mole) of 2,4,5-trifluoro-3-hydroxybenozic acid was added 40 ml of acetic anhydride, and the mixture was stirred for 15 hours under reflux. The reaction mixture was poured into ice-cold water, and then extracted with chloroform. The chloroform layer was washed with water, condensed under reduced pressure and the residue was washed with n-hexane to give 6.10 g of 3-acetoxy-2,4,5-trifluorobenzoic acid (V) as colorless powder.

Mass (CI): m/e 235 (M$^+$+1), 217 (M$^+$—OH), 175 (M$^+$—CH$_3$COO)

[Steps 2, 3, 4, 5 and 6]

In 200 ml of benzene was dissolved 6.10 g (0.026 mole) of 3-acetoxy-2,4,5-trifluorobenzoic acid (V), and to the solution was added 15 ml of thionyl chloride and stirred for 4 hours under reflux. After completion of the reaction, benzene and excess thionyl chloride were completely distilled off under reduced pressure to give 3-acetoxy-2,4,5-trifluorobenzoyl chloride (VI).

On the other hand, to 100 ml of anhydrous diethyl ether were added 3.17 g (0.028 mole) of magnesium ethoxide and 4.30 g (0.027 mole) of diethyl malonate and refluxed for 3 hours to give a suspension of ethoxymagnesium malonic diethyl ester in diethylether. To the suspension was added dropwise a solution of the above acid chloride dissolved in 50 ml of anhydrous diethyl ether, and after completion of the dropwise addition, the mixture was further stirred for an hour at room temperature. After completion of the reaction, 1N hydrochloric acid was added to the mixture to made it acidic, and the mixture was extracted with ethyl acetate. The organic layer was washed with water and dried, and then the solvent was distilled under reduced pressure to give 10.39 g of diethyl 3-acetoxy-2,4,5-trifluorobenzoylmalonate (VII) as yellowish oily product.

Then, the yellowish oily product was dissolved in 120 ml of dioxane and 4.90 g (0.026 mole) of p-toluenesulfonic acid monohydrate was added to the mixture and refluxed for 15 hours. After completion of the reaction, dioxane was distilled under reduced pressure. To the residue were added 100 ml of water and 2.15 g (0.026 mole) of sodium hydrogen carbonate and the mixture was extracted with chloroform. The chloroform layer was washed with water, dried and then distilled under reduced pressure to give 7.64 g of ethyl 3-acetoxy-2,4,5-trifluorobenzoylacetate (VIII) as reddish oily product.

To 7.64 g (0.025 mole) of the ethyl 3-acetoxy-2,4,5-trifluorobenzoylacetate (VIII) thus obtained were added 20 ml of acetic anhydride and 6 ml of ortho-ethyl formate and the mixture was refluxed for 2 hours and then condensed under reduced pressure. The residue was dissolved in 50 ml of dichloromethane, added 1.91 g (0.026 mole) of DL-2-aminopropanol and allowed to stand over night. Dichloromethane was distilled under reduced pressure and the residue was applied to silica gel column chromatography (solvent: mixture of toluene:ethyl acetate=1:1) to give 4.37 g of the ethyl-2-(3-acetoxy-2,4,5-trifluorobenzoyl)-3-(2-hydroxy-1-methylethyl)aminoacrylate (X) as pale yellow oily product.

Mass: m/e 389 (M$^+$), 358 (M$^+$ — CH$_2$OH), 43(+$\overset{O}{\overset{\|}{C}}$CH$_3$)

[Step 7]

In 30 ml of dimethylformamide was dissolved 4.30 g of the ethyl-2-(3-acetoxy-2,4,5-trifluorobenzoyl)-3-(2-hydroxy-1-methylethyl)aminoacrylate (X) thus obtained and 1.92 g (0.033 mole) of potassium fluoride was added to the mixture and the mixture was stirred at 140° to 150° C. for 2 hours. After completion of the reaction, the solvent was distilled under reduced pressure. To the residue was added water and the mixture was extracted with dichloromethane, and the organic layer was washed with water, dried and then condensed under reduced pressure. Then, the residue was washed with ethanol, and the residue was recrystallized from acetone to give 1.40 g of ethyl-9,10-difluoro-3-methyl-7-oxo-2,3-dihydro-7H-pyrido[1,2,3-de][1,4]benzoxazine-6-carboxylate (IV) as pale brown fine needle crystals.

M.p.: 255° to 256° C.

Elemental analysis (%): as C$_{15}$H$_{13}$F$_2$NO$_4$

|  | C | H | N |
| --- | --- | --- | --- |
| Theoretical value | 58.25 | 4.24 | 4.53 |
| Observed value | 58.09 | 4.14 | 4.24 |

According to the present invention, a novel compound 2,4,5-trifluoro-3-hydroxybenzoic acid useful as the synthetic intermediate for quinolone carboxylic acid derivatives which is useful as antibacterial agents can be provided, and the preparation steps of said quinolone carboxylic acid derivatives can be shortened to a great extent by use of said compound.

Also, according to the present invention, 3,5,6-trifluoro-4-hydroxyphthalic acid can be obtained at high yield.

We claim:

1. 2,4,5-Trifluoro-3-hydroxybenzoic acid represented by the following formula (I):

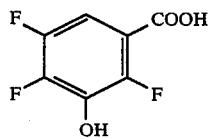
(I)

or a salt thereof.

2. The compound according to claim 1, wherein said salt is those selected from the group consisting of a lithium salt, sodium salt, potassium salt and calcium salt.

3. A process for preparing a 2,4,5-trifluoro-3-hydroxybenzoic acid represented by the following formula (I):

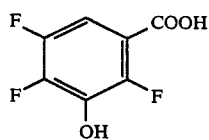
(I)

or a salt thereof, which comprises hydrolyzing a compound represented by the following formula (II):

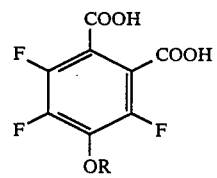
(II)

wherein R represents a hydrogen atom or an organic group capable of forming a hydroxyl group by hydrolysis, in water or an aqueous solvent at a temperature of 80° to 230° C.

4. The process according to claim 3, wherein the organic group capable of forming a hydroxyl group represented by R is an alkyl group having 1 to 6 carbon atoms, an aralkyl group having 7 to 10 carbon atoms, a cycloalkyl group having 5 to 10 carbon atoms or an acyl group having 1 to 10 carbon atoms.

5. The process according to claim 3, wherein said compound of the formula (II) is selected from the group consisting of 3,5,6-trifluoro-4-hydroxyphthalic acid, 3,5,6-trifluoro-4-methoxyphthalic acid, 3,5,6-trifluoro-4-ethoxyphthalic acid, 3,5,6-trifluoro-4-propoxyphthalic acid, 3,5,6-trifluoro-4-butoxyphthalic acid, 3,5,6-trifluoro-4-benzyloxyphthalic acid, 3,5,6-trifluoro-4-acetoxyphthalic acid and 3,5,6-trifluoro-4-benzoyloxyphthalic acid.

6. A process for preparing 3,5,6-trifluoro-4-hydroxyphthalic acid, which comprises allowing 3,4,5,6-tetrafluorophthalic acid to react with an alkaline compound in water or an aqueous solvent at 70° to 120° C., and then neutralizing the reaction product with an acidic aqueous solution and recovering the 3,5,6-trifluoro-4-hydroxy-phthalic acid.

7. The process according to claim 6, wherein the alkaline compound is an alkali metal hydroxide, hydrogen carbonate or carbonate.

8. The 2,4,5-trifluoro-3-hydroxybenzoic acid of claim 1.

9. The lithium salt of claim 2.

10. The sodium salt of claim 2.

11. The potassium salt of claim 2.

12. The calcium salt of claim 2.

13. The process of claim 7 wherein the alkaline compound is lithium hydroxide, sodium hydroxide, cesium hydroxide, potassium hydrogen carbonate or sodium hydrogen carbonate.

14. The process of claim 13, wherein said alkaline compound is present in the reaction mixture in an amount of from 5 to 40% by weight.

* * * * *